US006891178B2

(12) United States Patent
Xing (10) Patent No.: US 6,891,178 B2
(45) Date of Patent: May 10, 2005

(54) METHOD FOR CHECKING POSITIONAL ACCURACY OF THE LEAVES OF A MULTILEAF COLLIMATOR

(75) Inventor: Lei Xing, Stanford, CA (US)

(73) Assignee: The Board of Trustees of the Lealand Stanford Junior University, Palo Alto, CA (US)

( * ) Notice: Subject to any disclaimer, the term of this patent is extended or adjusted under 35 U.S.C. 154(b) by 408 days.

(21) Appl. No.: 10/197,232

(22) Filed: Jul. 15, 2002

(65) Prior Publication Data

US 2003/0031298 A1 Feb. 13, 2003

Related U.S. Application Data

(60) Provisional application No. 60/306,736, filed on Jul. 19, 2001.

(51) Int. Cl.[7] ............................. G21K 1/02; A61N 5/10
(52) U.S. Cl. ............................. 250/505.1; 250/503.1; 250/496.1; 250/515.1; 250/397; 378/147
(58) Field of Search ............................ 250/505.1, 503.1, 250/496.1, 515.1, 397; 378/147

(56) References Cited

U.S. PATENT DOCUMENTS

| | | | | | |
|---|---|---|---|---|---|
| 5,754,623 | A | * | 5/1998 | Seki ............................ | 378/65 |
| 2003/0174808 | A1 | * | 9/2003 | Hughes et al. ................ | 378/65 |
| 2003/0191384 | A1 | * | 10/2003 | Svatos et al. ................ | 600/410 |

OTHER PUBLICATIONS

LoSasso T, Chui CS & Ling CC, (1998), "Physical and dosimetric aspects of a multileaf collimation system used in the dynamic mode for implementing intensity modulated radiotherapy," Med. Phys., 25:1919–1927.

Budgell GJ, Mott JHL, Williams PC & Brown KJ, (2000), "Requirements for leaf positioning accuracy for dynamic multileaf," Phys. Med. Biol., 45:1211–1227.

Zygmanski P & Kung JH, (2001), "Method of identifying dynamic multileaf collimator irradiation that is highly sensitive to a systematic MLC calibration error," Med. Phys., 28:2220–2226.

Graves MN, Thompson AV, Martel MK, McShan DL & Fraass BA, (2001), "Calibration and quality assurance for round leaf–end systems," Med. Phys., 28:2227–2233.

Low W, Sohn JW, Klein EE, Markman J, Mutic S & Dempsey JF, (2001), "Characterization of a commerical multileaf collimator used for intensity modulated radiation therapy," Med. Phys., 28:752–756.

Chui CS, Sprirou S & LoSasso T, (1996), "Testing of dynamic multileaf collimation," Med. Phys., 23, 635–641.

LoSasso T, Chui CS & Ling CC, (2001), "Comprehensive quality assurance for the delivery of intensity modulated radiotherapy with a multileaf collimator used in the dynamic mode," Med. Phys., 28:2209–2219.

* cited by examiner

*Primary Examiner*—Nikita Wells
(74) *Attorney, Agent, or Firm*—Lumen Intellectual Property Services, Inc.

(57) ABSTRACT

A method is provided for determining the positional accuracy of leaves of a multileaf collimator for delivering doses of radiation to a particular spatial location for treatment purpose. The method could be implemented as routine quality assurance check of the multileaf collimator leaf positioning errors. The method includes producing a first field and producing a second field, which is different from the first field. A dosimeter means is included for measuring a radiation dose difference or ratio between the first field and the second field at at least one spatial location. The dose difference or ratio is then used to determine the positional accuracy of the leaves by comparing with a known relationship between leaf positional errors and relative dosimeter outputs. The method provides a more simplified, accurate, efficient and reliable method over currently used methods.

14 Claims, 7 Drawing Sheets

METHOD FOR CHECKING POSITIONAL ACCURACY OF THE LEAVES OF A MULTILEAF COLLIMATOR

CROSS-REFERENCE TO RELATED APPLICATIONS

This application is cross-referenced to and claims priority from U.S. Provisional Application No. 60/306,736 filed on Jul. 19, 2001, which is hereby incorporated by reference.

FIELD OF THE INVENTION

The present invention relates generally to multileaf collimators used to deliver therapeutic radiation doses. More particularly, the present invention relates to a method to check positional accuracy of the leaves of a multileaf collimator in intensity modulated radiation therapy.

BACKGROUND

Intensity modulated radiation therapy (IMRT) is an advanced form of radiation therapy. In IMRT using multileaf collimators, it is critical for the MLC leaves to move accurately according to the pre-designed trajectories to achieve the planned radiation dose distribution with certain accuracy. In contrast to conventional methods, IMRT requires a much more stringent quality assurance (QA) to ensure the normal operation of the delivery system. One of the main quality assurance (QA) tasks is the assurance of positional accuracy of the multileaf collimator leaves. Several studies have indicated that the dose delivery accuracy of IMRT is highly sensitive to multileaf collimator leaf positioning error (See e.g. LoSasso T, Chui C S & Ling C C (1998) *Physical and dosimetric aspects of a multileaf collimation system used in the dynamic mode for implementing intensity modulated radiotherapy,* Med. Phys. 25:1919–1927; Budgell G J, Mott J H L, Williams P C & Brown K J (2000), *Requirements for leaf positioning accuracy for dynamic multileaf,* Phys. Med. Biol. 45:1211–1227). For instance, an error of about 1.0 mm in leaf position could result in more that 10% dose error. Multileaf collimator leaf errors can generally be classified into systematic errors and random errors. A systematic error is referred to as a constant error of all leaves at every leaf position. A random is referred to as an error that may occur at any leaf with an arbitrary value in a certain range. There are two main sources of systematic multileaf collimator leaf position errors, i.e. centerline mechanical offset and imprecise determination of radiation field offset in case of a rounded end MLC (See e.g. Zygmanski P & Kung J H (2001), *Method of identifying dynamic multileaf collimator irradiation that is highly sensitive to a systematic MLC calibration error,* Med. Phys. 28:2220–2226).

Several methods have been employed to identify and correct the systematic errors; accuracies of better than 3 mm can be obtained (See e.g. LoSasso T, Chui C S & Ling C C (1998), *Physical and dosimetric aspects of a multileaf collimation system used in the dynamic mode for implementing intensity modulated radiotherapy,* Med. Phys. 25:1919–1927; Graves M N, Thompson A V, Martel M K, McShan D L & Fraass B A (2001), *Calibration and quality assurance for rounded leaf-end systems,* Med. Phys. 28:2227–2233; Low W, Sohn J W, Klein E E, Markman J, Mutic S & Dempsey J F (2001), *Characterization of a commercial multileaf collimator used for intensity modulated radiation therapy,* Med. Phys. 28:752–756). Sources that may affect the magnitude of a random leaf position error include the precision of the multileaf collimator control system, the absolute accuracy of calibration of the multileaf collimator leaf positions and the stability of leaf drive motors. For a multileaf collimator system, a systematic error is relatively easy to handle and once a systematic error is corrected in the system, it would not be necessary to check such an error if the conventional alignment of light fields and radiation fields is performed periodically. On the other hand, a random multileaf collimator leaf positioning error check should be performed on a more regular basis since it is unknown when such an error occurs in a particular leaf.

Currently, in most clinics, the routine QA of MLC is performed using radiographic films with specifically designed MLC leaf sequences as described by Chui et al. (Chui C S, Sprirou S & LoSasso T (1996), *Testing of dynamic miltileaf collimation,* Med. Phys. 23, 635–641; LoSasso T, Chui C S & Ling C C (2001), *Comprehensive quality assurance for the delivery of intensity modulated radiotherapy with a multileaf collimator used in the dynamic mode,* Med. Phys. 28:2209–2219). In the method taught by Chui et al., a film is exposed to a dynamically delivered multileaf collimator field that produces a matrix of high intensity regions, for instance about 1 mm wide and 2 cm apart. Subsequently, the film is evaluated for irregularities of the high intensity regions caused by potential leaf positioning inaccuracy. With this method, it is believed possible to visually detect leaf positioning errors as small as about 0.2 mm. However, such a QA performance test is time consuming due to the overhead associated with film irradiation and processing. Furthermore, the film measurement results are difficult to interpret and quantify. Therefore it would, for instance, be difficult to detect errors less than 0.2 mm, which renders the method of film measurement inadequate for QA in IMRT. Accordingly, there is a need to develop new and more accurate methods to improve QA in IMRT.

SUMMARY OF THE INVENTION

The present invention provides a method for determining the positional accuracy of leaves of a multileaf collimator. The method includes producing a first field and producing a second field, which is different from the first field. A dosimeter means is included for measuring a radiation dose difference or ratio between the first field and the second field at at least one spatial location. The dose difference or ratio is then used to determine the positional accuracy of the leaves by comparing the dose difference or ratio with a known relationship between leaf positional errors and relative dosimeter outputs.

The present invention teaches different embodiments to obtain the first and second reading. A first embodiment shows the first field as is an open field and the second field as a partial field based on the settings of the leaves of the multileaf collimator. The open field is used as a reference for the partial field. Once the open field measurement is known, it would also be possible and sufficient to simply provide this open field as a measurement to determine the difference or ratio with the partial field. Another embodiment shows the first field being produced based on a first setting of the leaves of the multileaf collimator and the second field being produced based on a second setting of the leaves of the multileaf collimator whereby the second setting being inverse from the first setting. In this case both leaves settings are used as references to each other. Yet another embodiment in which both fields are used as reference to each other shows the first field being a wedge field and second field being the inverse of that wedge field. Still another embodiment shows the first field being determined using a calibrated collimator whereby the calibrated collimator provides a reference to the second field which is based on a setting of the leaves of a multileaf collimator.

In view of that which is stated above, it is the objective of the present invention to provide a method that determines the positional errors of leaves in a multileaf collimator.

It is another objective of the present invention to provide a method for checking the positional errors of leaves in a multileaf collimator that can be used as a routine check for quality assurance measurements.

The advantage of the present invention is that is provides a more simplified and more accurate method over currently used methods. The method is efficient and reliable in determining possible positional errors of leaves in a multileaf collimator.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Figure 1:
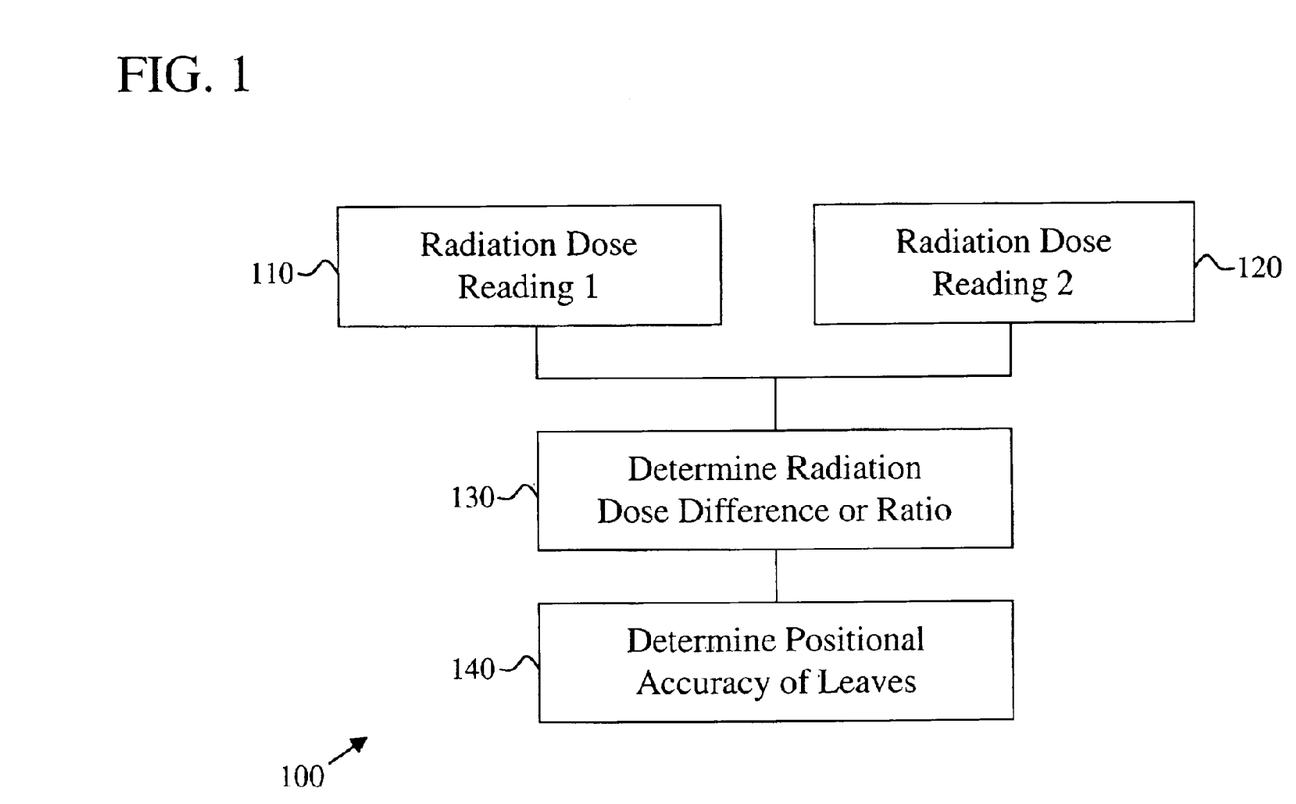
FIG. 1 shows an overview of the method according to the present invention.
Figure 2:
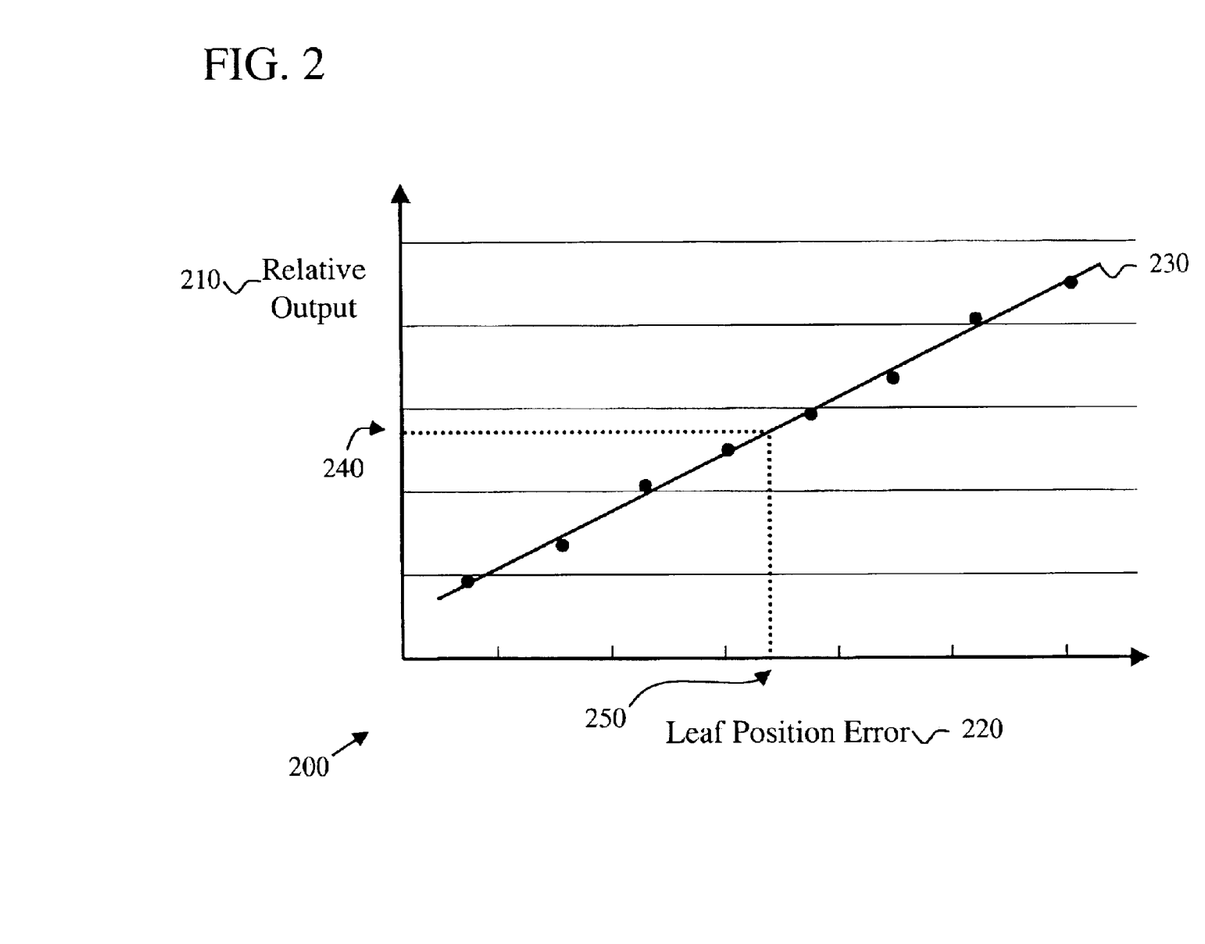
FIG. 2 shows an exemplary relationship of relative output of the dosimeter means and leaf positional errors according to the present invention.

The present invention provides a method for determining the positional accuracy of leaves of a multileaf collimator for delivering doses of radiation to a particular spatial location for treatment purposes, e.g., for delivering radiation doses to treat tumors. The method of the present invention could be implemented as a method for routine QA of the multileaf collimator leaf positioning. FIG. 1 shows an overview 100 of the steps of the present method for determining the positional accuracy of the leaves of a multileaf collimator. The method includes two different radiation dose readings or measurements, i.e. 110 and 120, of a field that are compared to each other. The first field measurement could be performed just before the second measurement, but could also be done at an earlier stage. Furthermore, the second field measurement could be a static or a dynamic field. A dosimeter means is used for measuring a radiation dose difference or ratio 130 between the first field reading 110 and the second field reading 120 at at least one spatial location in the field. The method can be used to detect the positional accuracy of a leaf at an arbitrary spatial location and does not have to be at the central position (See FIGS. 3–7). In general, the difference could be determined from a fluence or an intensity. Different dosimeter means can be used such as, for instance, but not limited to, a single finite-sized dosimeter, a collection of small dosimeters at a small area, an array of dosimeters or an ion chamber. Other dosimeters/imaging devices known in the art to radiation measure radiation could also be used. For instance, dosimeters like electronic portal imaging devices (EPIDs) either camera based, amorphous silicon based, or matrix ion chamber based could be used. A typical imaging device includes either "continuous" (optical or camera based imager) or a dense (with a spacing of less than a few hundred microns) array of detectors (semiconductor or liquid ion chamber). When dosimeter means is placed under a radiation beam, the integral signal (or dose) over a small area at a specific point is equivalent to the reading from a finite-sized detector at that location. This would allow the method of the present invention to be applied directly to MLC leaf positioning check based on a dosimeter means. Once the difference or ratio between the two radiation dose readings is established the positional accuracy 140 of the leaves could be determined. For instance, the positional accuracy could be determined by looking up in a data set, data plot or a graph of the relative output 210 versus the leaf displacement 220. Such a data set, data plot or a graph could have been established by previous calibration tests or is known for the particular multileaf collimator that is being tested. An example of such a graph is shown in FIG. 2 by graph 200 in which data points of the relative output and leaf positional errors were fitted to a linear relationship 230. However, any other form or relationship would also be possible and the present invention is not limited to a linear relationship, since the relationship is dependent on the type of multileaf collimator and type of detector. Once the relationship between the relative output 220 or difference versus leaf displacement has been established, see e.g. graph 200, the leaf positional error could be determined and quantified as is shown, for illustrative purposes only, for relative output 240 which determines leaf positional error 250.

Figure 3:
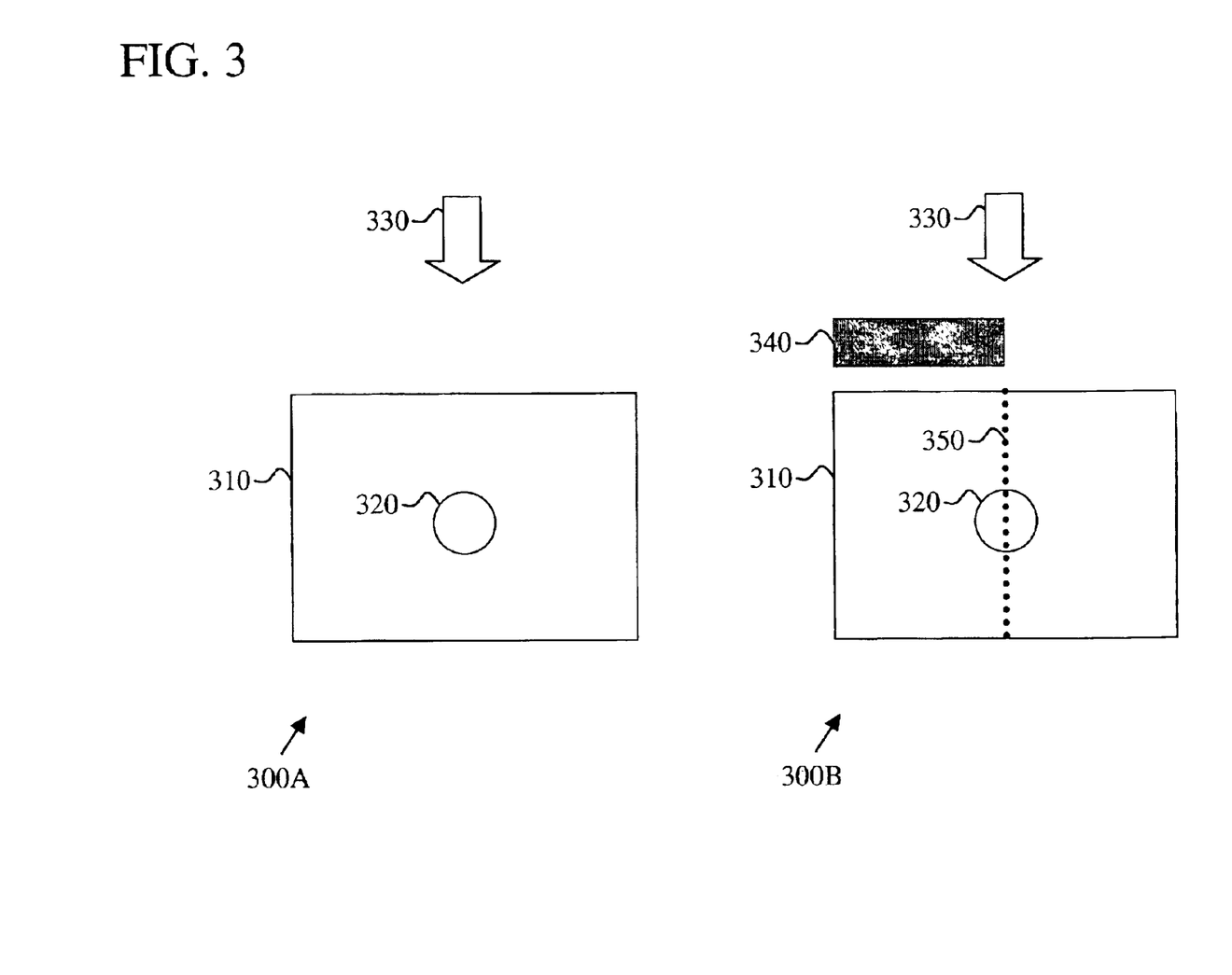
FIGS. 3–7 show exemplary embodiments of methods for determining positional accuracy of one or more leaves of a multileaf collimator according to the present invention.

FIG. 3 shows one embodiment according to the present invention in which a volumetric field 310 is used to determine a first reading 300A and a second reading 300B. For illustrative purposes, field 310 includes one dosimeter 320 that is used to determine the radiation dose from radiation source 330. In this particular embodiment shown by 300A, the leaves of a multileaf collimator are set in a position or sequence such that an open field could be produced. For the second reading as shown in 300B, leaf 340 of a multileaf collimator is set in a position or sequence such that a partial open field could be produced. In this particular example, leaf 340 is positioned to verify the positional accuracy around the central axis 350 of dosimeter 320. However, as a person of average skill in the art would readily appreciate, the positional accuracy of leaf 340 could also be determined at any position of leaf 340 that is off the central axis 350 of dosimeter 320. Dosimeter 320 obtains two different readings or radiation dose measurements, which could be compared as a difference, ratio or other mathematical means. If the position of leaf 320 is inaccurate, then the difference will indicate whether the second reading in 300B is higher or lower than it ought to be. In this particular embodiment, the open field is used as a reference field. As a person of average skill in the art would readily recognize, instead of measuring the open field, the open field could also be known based on a previous measurement. In that case there would be no need for measuring the open field radiation dose. In that case, one only needs to measure a partial field, which is then compared with the open field value to determine the positional errors of the leaves.

The following is an example of how one could determine the positional error based on the embodiment of FIG. 3. Assume that the previously determined calibration curve for a given multileaf collimator and detector is linear and is given by R=aE+b, with a=0.5702 (cm$^{-1}$) and b=0.0866, where F is positional error and R is the relative output of a field shaped by leaf. When performing QA check of leaf 340 according to the setup in FIG. 3, one measures the (first) open field 300A and the (second) leaf field 300B. The ratio of the two readings of dosimeter means 320 gives the R in the above formula. Substitute the value R into the above formula and one will obtain the positional error E=(R−0.0866)/0.5702. If R=0.0866, E=0, which means that the leaf is in the desired position. Otherwise, there is an error in the positioning of the leaf. For example, if R=0.0800, there is an error E=0.0116 cm.

Figure 4:
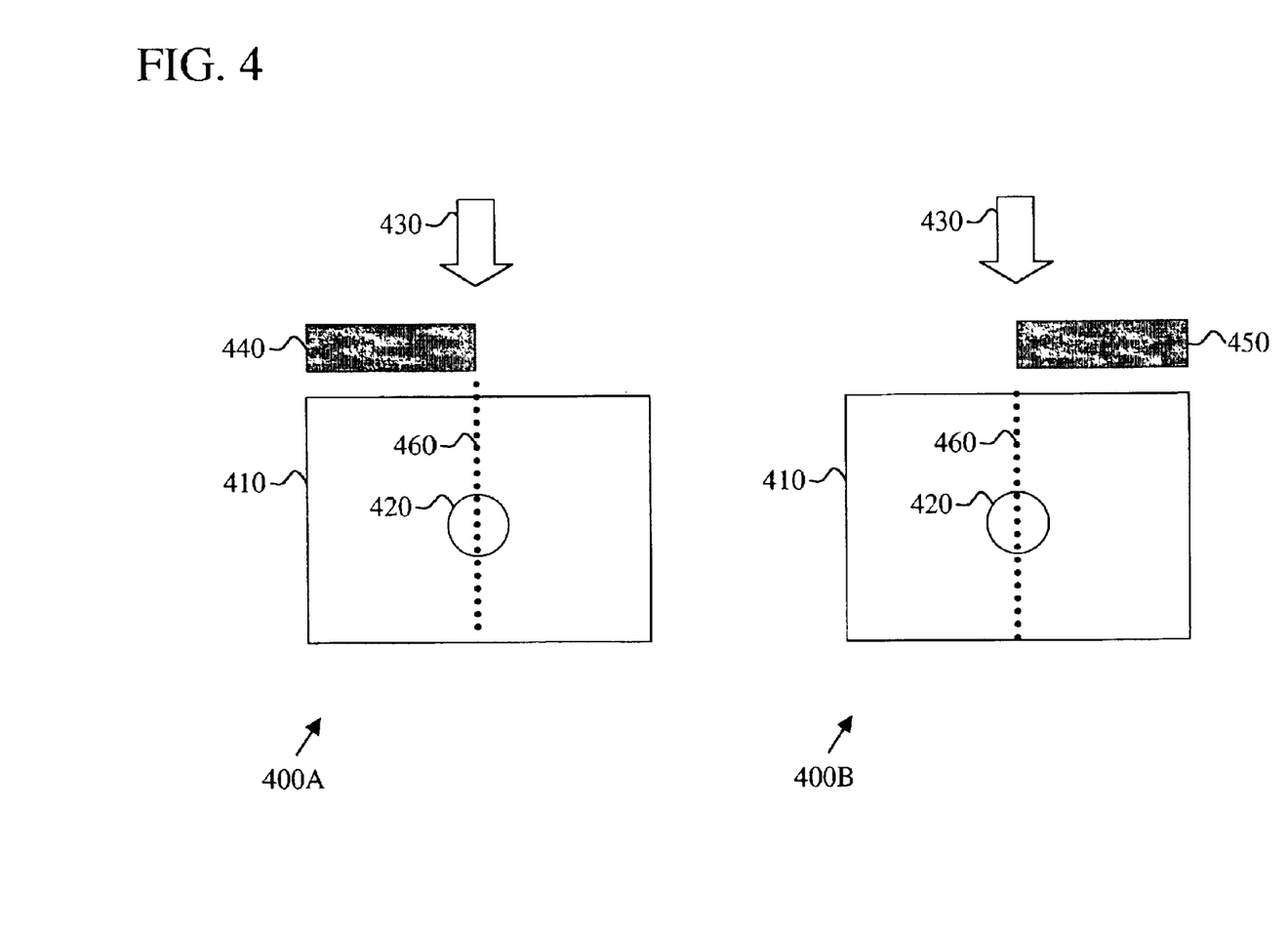

FIG. 4 shows another embodiment according to the present invention in which a volumetric field 410 is used to determine a first reading 400A and a second reading 400B. For illustrative purposes, field 410 includes one dosimeter 420 that is used to determine the radiation dose from radiation source 430. In this particular embodiment shown by 400A, leaf 440 of a multileaf collimator is set in a position or sequence such that a partial field could be produced. For the second reading as shown in 400B, leaf 450 of a multileaf collimator is set in a position or sequence such that a partial open field could be produced which is the inverse of the partial field in 400A produced by leaf 440. In this particular example, leaves 440, 450 are positioned to verify the positional accuracy around the central axis 460 of dosimeter 420. However, as a person of average skill in the art would readily appreciate, the positional accuracy of leaves 440, 450 could also be determined at any position of leaves 440, 450 that is off the central axis 450 of dosimeter 420. The key idea here is that the first reading and the second reading are not only different from each other but also have an inverse relationship as shown in FIG. 4. The determination of the positional accuracy here takes advantage of the symmetry and asymmetry of the leaves. Dosimeter 420 obtains two different readings or radiation dose measurements, which could be compared as a difference, ratio or other mathematical means. If the position of leaves 440, 450 is inaccurate, then the difference will indicate the degree of positional inaccuracy of the leaves of the multileaf collimator.

Figure 5:
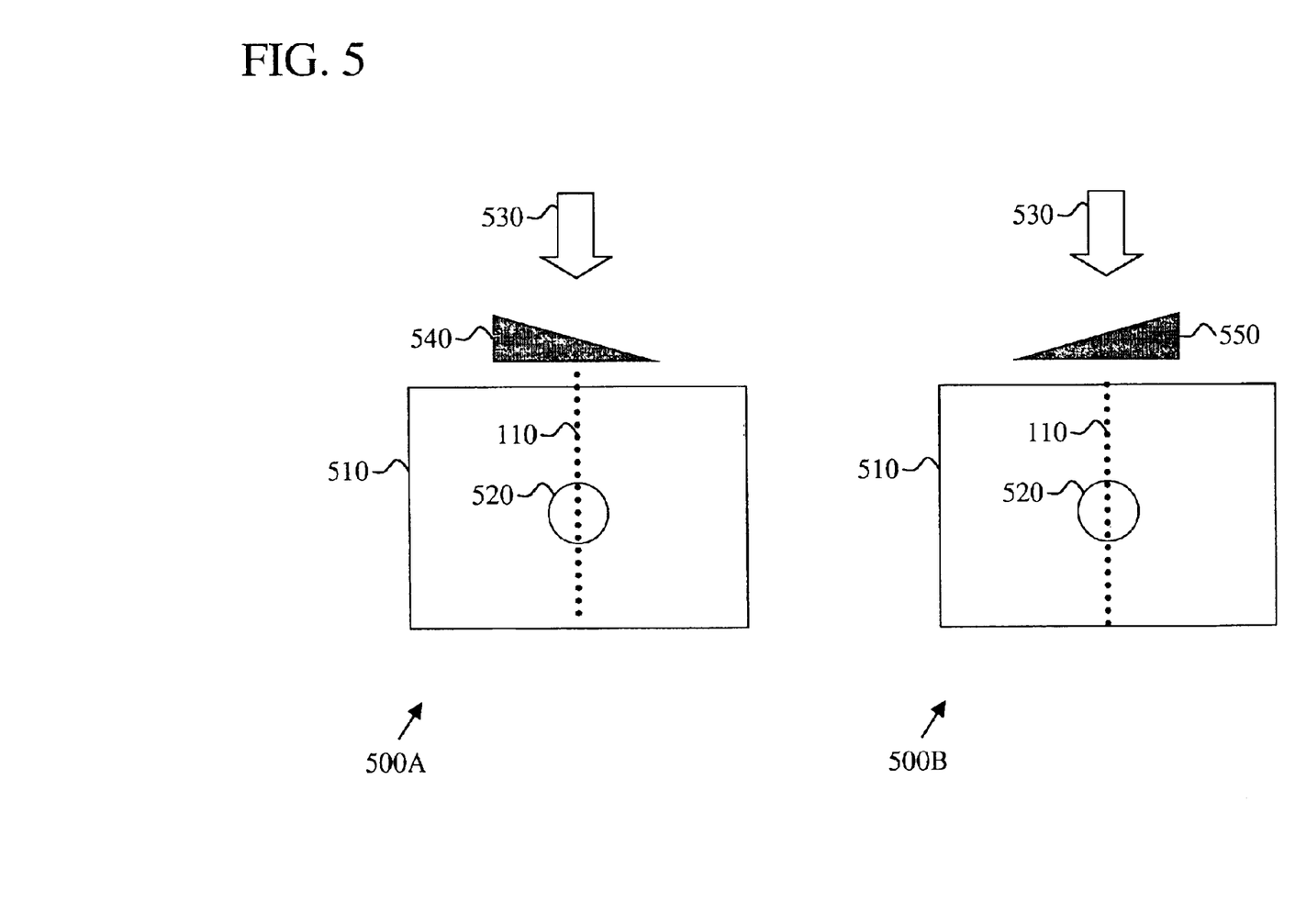

FIG. 5 shows yet another embodiment according to the present invention in which a multileaf collimator wedge field is used in a volumetric field 510 to determine a first reading 500A and a second reading 500B. For illustrative purposes, field 510 includes one dosimeter 520 that is used to determine the radiation dose from radiation source 530. In this particular embodiment shown by 500A, wedge 540 is set in a position or sequence such that a partial field could be produced. For the second reading as shown in 500B, wedge 550 of a multileaf collimator is set in a position or sequence such that a partial open field could be produced which is the inverse of the partial field in 500A produced by wedge 540. The key idea here is that the first reading and the second reading are not only different from each other but also have an inverse relationship as shown in FIG. 5. The determination of the positional accuracy here takes advantage of the symmetry and asymmetry of the wedges. Dosimeter 520 obtains two different readings or radiation dose measurements, which could be compared as a difference, ratio or other mathematical means. If the position of wedges 540, 550 is inaccurate, then the difference will indicate a positional inaccuracy of the leaves of the multileaf collimator. Different wedges could be used such as a phantom material wedge, metal wedge, step-wise field or the like.

Figure 6:
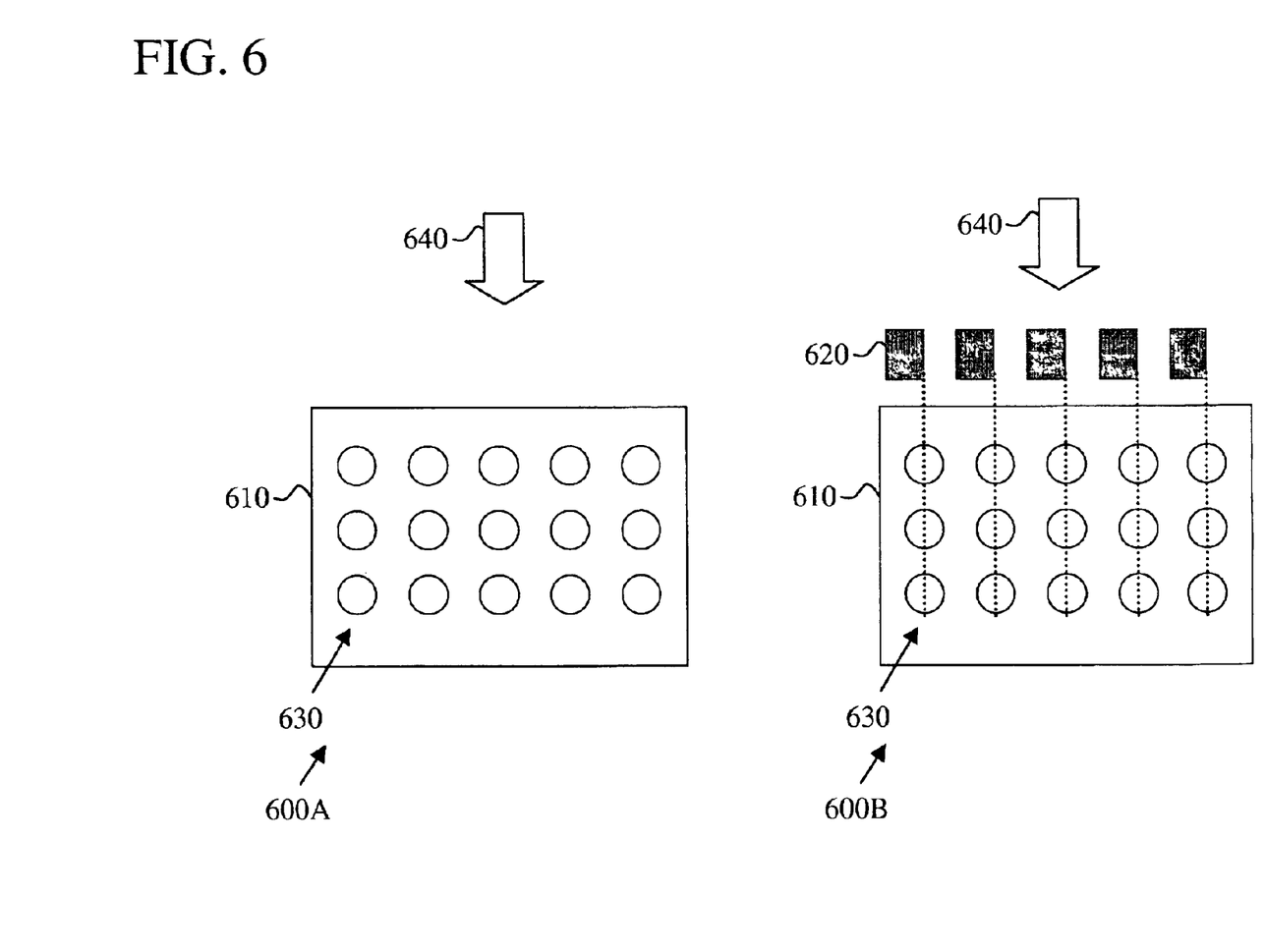

FIG. 6 shows another embodiment according to the present invention in which a volumetric field 610 is used to determine a first reading 600A and a second reading 600B and determine the position accuracy of a plurality of leaves 620 in a multileaf collimator with an array of dosimeters 610 and radiation source 630. In this particular example of FIG. 6 the first reading pertains an open field reading and the second reading pertains a partial open field reading according to the position of the leaves.

Figure 7:
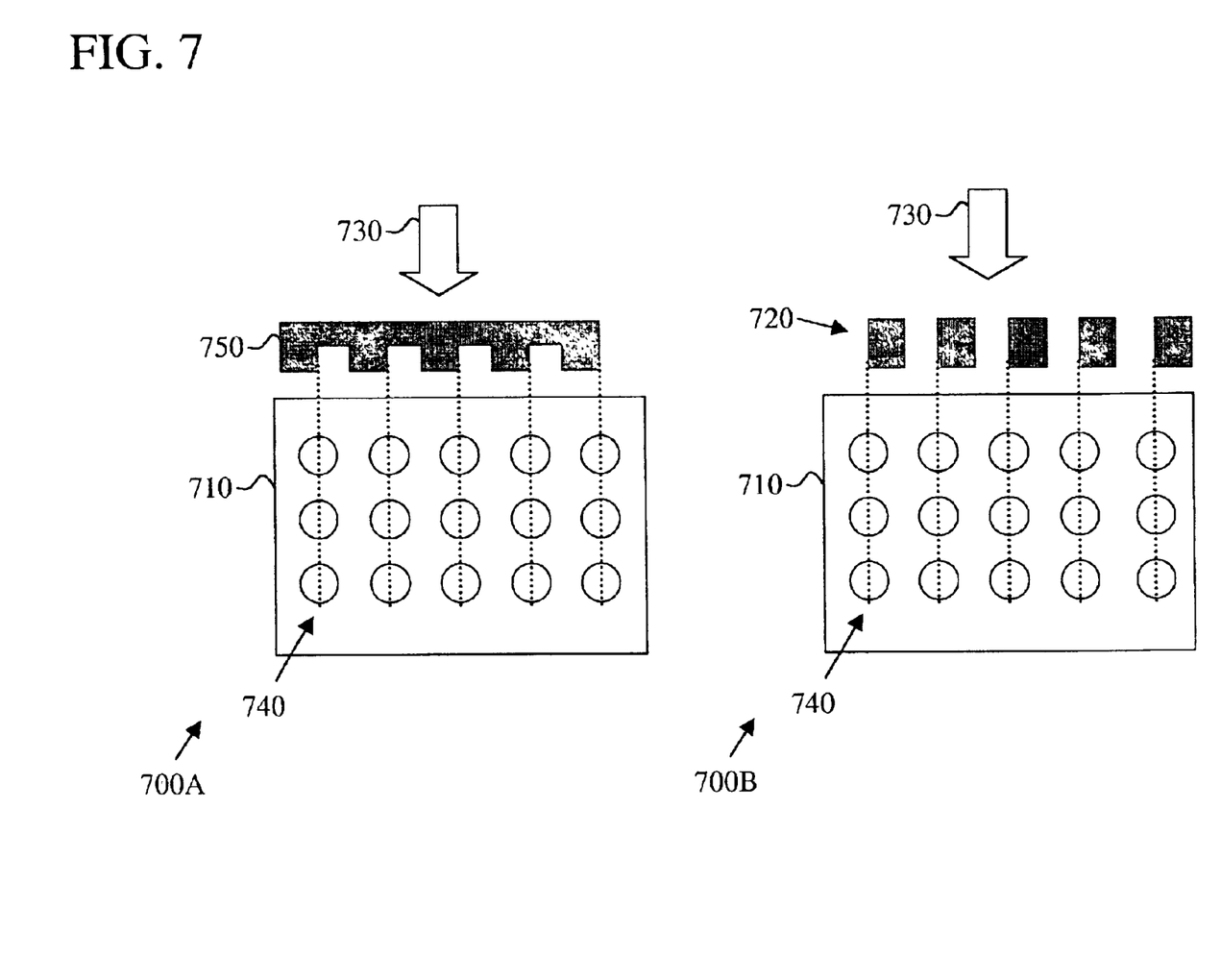

FIG. 7 shows another embodiment according to the present invention in which a volumetric field 710 is used to determine first readings 700A and second readings 700B and determine the position accuracy of a plurality of leaves 720 in a multileaf collimator with an array of dosimeters 710. In this particular example of FIG. 7 the first reading includes a calibrated collimator 750 to obtain a calibrated reading and the second reading pertains a partial open field reading according to the position of the leaves. Calibrated collimator 750 is, for instance, a calibrated metal strip with different thickness, that allows collimating the radiation from radiation source 730 to dosimeters 740 through the thinner part of calibrated collimator 750. The key idea here is that the first readings and the second readings are not only different from each other but also have an inverse relationship as shown in FIG. 7. The determination of the positional accuracy here takes advantage of the symmetry and asymmetry of the calibrated collimator and the leaves. Dosimeters 710 obtained different readings or radiation dose measurements, which could be compared as differences, ratios or other mathematical means. If the position of leaves 720 is inaccurate, then the difference will indicate the degree of positional inaccuracy of leaves 720 of the multileaf collimator.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the present invention could be modified to check gantry angle accuracy in conformal arc therapy or intensity modulated arc therapy. Yet another way that the present method could be modified is to check dynamic wedge positional accuracy. All such variations are considered to be within the scope and spirit of the present invention as defined by the following claims and their legal equivalents.

What is claimed is:

1. A method for determining the positional accuracy of leaves of a multileaf collimator, said method comprising:
    a) producing a first field;
    b) producing a second field, wherein said second field is different from said first field;
    c) providing a dosimeter means for measuring a radiation dose difference or ratio between said first field and said second field at least one spatial location; and
    d) determining the positional accuracy of said leaves from said difference.

2. The method as set forth in claim 1, wherein said first field is an open field, and wherein said step of producing said second field comprises the step of setting said leaves of said collimator in a sequence, wherein said sequence produces a partial field.

3. The method as set forth in claim 1, wherein said step of producing said first field comprises the step of setting said leaves of said multileaf collimator in a first sequence, and wherein said step of producing said second field comprises the step of setting said leaves of said multileaf collimator in a second sequence, wherein said second sequence is inverse from said first sequence.

4. The method as set forth in claim 1, wherein said step of producing said first field comprises the step of using a calibrated collimator wherein said collimator produces a first sequence, and wherein said step of producing said second field comprises the step of setting said leaves of said multileaf collimator in a second sequence, wherein said sequence is inverse from said first sequence.

5. The method as set forth in claim 1, wherein said first field is a wedge field and said second field is the inverse of said wedge field.

6. The method as set forth in claim 1, wherein said first field is a calibrated field.

7. The method as set forth in claim 1, wherein said dosimeter means comprises a dosimeter with a line, said difference being determined at said line.

8. The method as set forth in claim 7, wherein said line is a central line.

9. The method as set forth in claim 1, wherein said difference is determined from a fluence.

10. The method as set forth in claim 1, wherein said difference is determined from an intensity.

11. The method as set forth in claim 1, wherein said dosimeter means comprise an array of dosimeters.

12. The method as set forth in claim 1, wherein said dosimeter means comprise at least one symmetric detector.

13. The method as set forth in claim 1, wherein said dosimeter means comprise an ion chamber.

14. A method for determining the positional accuracy of leaves of a multileaf collimator, said method comprising:
   a) providing an open field measurement;
   b) setting said leaves in a sequence such that said multileaf collimator produces a partial field;
   c) providing a dosimeter means for measuring a radiation dose difference or ratio between said open field measurement and said partial field at at least one spatial location; and
   d) determining the positional accuracy of said leaves from said difference.

* * * * *